(12) United States Patent
Bradley et al.

(10) Patent No.: US 7,270,580 B2
(45) Date of Patent: Sep. 18, 2007

(54) METHODS AND APPARATUS FOR CONDUCTING ELECTRICAL CURRENT

(75) Inventors: Patrick Walton Bradley, Cardiff-by-the-Sea, CA (US); Gail Dawn Baura, San Diego, CA (US)

(73) Assignee: Cardio Dynamics International Corporation, San Diego, CA (US)

( * ) Notice: Subject to any disclaimer, the term of this patent is extended or adjusted under 35 U.S.C. 154(b) by 0 days.

(21) Appl. No.: 11/343,839

(22) Filed: Jan. 31, 2006

(65) Prior Publication Data

US 2006/0128193 A1    Jun. 15, 2006

(51) Int. Cl.
*H01R 4/48* (2006.01)
(52) U.S. Cl. .......................... 439/729; 439/909
(58) Field of Classification Search ................ 439/268, 439/729, 819, 822, 859, 909, 910, 930
See application file for complete search history.

(56) References Cited

U.S. PATENT DOCUMENTS

| | | | |
|---|---|---|---|
| 4,299,231 A | 11/1981 | Karmann et al. | |
| 4,331,153 A | 5/1982 | Healy | |
| 5,184,620 A | 2/1993 | Cudahy et al. | |
| 5,562,607 A * | 10/1996 | Gyory | ............... 604/20 |
| 5,645,063 A | 7/1997 | Straka, Jr. | |
| 5,660,177 A | 8/1997 | Faupel et al. | |
| 5,895,298 A | 4/1999 | Faupel et al. | |
| 6,064,901 A * | 5/2000 | Cartmell et al. | ............ 600/372 |
| D468,433 S | 1/2003 | Wagner et al. | |
| D471,281 S | 3/2003 | Baura et al. | |
| D475,138 S | 5/2003 | Baura et al. | |
| 6,561,986 B2 | 5/2003 | Baura et al. | |
| 6,602,201 B1 | 8/2003 | Hepp et al. | |
| 6,636,754 B1 | 10/2003 | Baura et al. | |

OTHER PUBLICATIONS

European Search Report and Opinion, European Patent Office, International Appln. No. PCT/US06/33583, Date of Completion of Search Feb. 2, 2007.

* cited by examiner

*Primary Examiner*—Khiem Nguyen
(74) *Attorney, Agent, or Firm*—Robert B. Reeser, III; Armstrong Teasdale LLP

(57) ABSTRACT

An electrode assembly for use with a living subject includes a substrate having first and second openings extending therethrough, and a first terminal at least partially received within the first opening. The first terminal includes an end portion having a first size. At least a portion of the first terminal configured to conduct electrical current. A second terminal is at least partially received within the second opening. The second terminal includes an end portion having a second size that is different than the first size of the first terminal end portion. At least a portion of the second terminal is configured to conduct electrical current. The assembly also includes a first electrolytic element configured to transfer electrical current between the skin of a living subject and the first terminal, and a second electrolytic element configured to transfer electrical current between the skin of a living subject and the second terminal.

21 Claims, 10 Drawing Sheets

METHODS AND APPARATUS FOR
CONDUCTING ELECTRICAL CURRENT

BACKGROUND OF THE INVENTION

This invention relates generally to biomedical analysis, and more specifically to methods and apparatus for conducting electrical current through a living subject to determine a property of the living subject.

At least some known methods use impedance cardiography to non-invasively determine cardiac output estimates. For example, impedance cardiography, sometimes referred to as thoracic bioimpedance or impedance plethysmography, may be used to measure the stroke volume of a heart. The stroke volume can then be multiplied by heart rate, for example obtained using an electrocardiogram (ECG), to obtain cardiac output. At least some known methods of measuring the stroke volume include modeling thoracic, or chest cavity, impedance $Z_T(t)$ as a constant impedance, $Z_0$, and as a time-varying impedance, $\Delta Z(t)$. Changes in the impedance over time can be related to a change in fluidic volume, and ultimately stoke volume and cardiac output.

In at least some known methods, impedance is measured using an impedance waveform derived from two or more electrode assemblies placed at different locations on the living subject's body. The electrode assemblies include a stimulation terminal coupled to a current source and a measurement terminal coupled to a measurement device. AC electrical current supplied to the stimulation terminal flows from the stimulation terminal of a first electrode assembly through the living subject's body to the stimulation terminal of a second electrode assembly. Voltage at the measurement terminals of both electrode assemblies is then measured and used to obtain the thoracic impedance $Z_T(t)$. Known measurement and stimulation terminals are generally the same standard size on each electrode. For example, known electrode terminals generally accept identically sized electrical connectors from the current source or measurement device, respectively. However, because the electrode terminals are the same size, connectors may be inadvertently coupled to the wrong electrode terminal, such that the circuit is reversed. More specifically, the electrical connector coupled to the current source may be inadvertently coupled to the measurement terminal and the electrical connector coupled to the measurement device may be inadvertently coupled to the stimulation terminal. Coupling the electrical connectors to the wrong terminal may decrease an accuracy of the impedance measurement, which may decrease an accuracy of the determined cardiac output and/or may cause mismanagement of the living subject.

BRIEF DESCRIPTION OF THE INVENTION

In one aspect, an electrode assembly for use with a living subject includes a substrate having first and second openings extending therethrough, and a first terminal at least partially received within the first opening. The first terminal includes an end portion having a first size. At least a portion of the first terminal configured to conduct electrical current. A second terminal is at least partially received within the second opening. The second terminal includes an end portion having a second size that is different than the first size of the first terminal end portion. At least a portion of the second terminal is configured to conduct electrical current. The assembly also includes a first electrolytic element configured to transfer electrical current between the skin of a living subject and the first terminal, and a second electrolytic element configured to transfer electrical current between the skin of a living subject and the second terminal.

In another aspect, a system for determining a cardiac output of a living subject includes at least two electrode assemblies each including first and second terminals. The first terminals each include an end portion having a first size. The second terminals each include an end portion having a second size that is different from the first size of the first terminal end portions. At least a portion of each of the first and second terminals is configured to conduct electrical current. Each of the first terminals is configured to couple to an electrical current source. The system also includes a component coupled to each of the second terminals and configured to measure a difference in voltage between the second terminals induced from current flowing between the first terminals through at least a portion of the living subject.

In another aspect, a method is provided for determining a cardiac output of a living subject. The method includes providing at least two electrode assemblies each including first and second terminals, wherein the first terminals each include an end portion having a first size, and the second terminals each include an end portion having a second size that is different from the first size of the first terminal end portions, positioning the at least two electrode assemblies on the skin of the living subject, generating an electrical current passing between the first terminals of the at least two electrode assemblies at least partially through the living subject, measuring the voltage at each of the second terminals, determining a cardiac stroke volume from the measured voltages, and determining the cardiac output based at least in part on the determined cardiac stroke volume.

In another aspect, an electrical connector for electrically and mechanically coupling an electrical cable to a terminal includes a housing including at least one wall and an internal cavity at least partially defined by the at least one wall. The at least one wall includes a hole for receiving at least a portion of the terminal. A spring is positioned at least partially within the internal cavity and electrically coupleable to the electrical cable. The spring includes first and second arms each having a first portion and a second portion. The first portions define an opening positioned relative to the housing hole to receive at least a portion of the terminal when the terminal extends through the housing hole. The first portions are biased toward each other such that the first portions engage the terminal when the terminal is received within the opening to facilitate electrically coupling the terminal to the spring and to facilitate retaining the terminal within the opening. The first and second portions are configured such that when the first and second arm second portions move toward each other the first and second arm first portions move away from each other to enlarge the opening for receiving the terminal therethrough. At least one actuator is coupled to the housing in engagement with the first and second arm second portions. The at least one actuator is configured to move the first and second arm second portions toward each other.

In another aspect, an electrical connector for electrically and mechanically coupling an electrical cable to a terminal includes a housing including at least one wall and an internal cavity at least partially defined by the at least one wall. The at least one wall includes at least one hole for receiving at least a portion of the terminal. An engagement member is positioned at least partially within the internal cavity and is electrically coupleable to the electrical cable. The engagement member includes first and second openings each positioned relative to the at least one hole to receive at least a portion of the terminal when the terminal extends through the at least one hole. The engagement member is configured to engage the terminal when the terminal is received within the first opening to facilitate electrically coupling the terminal to the engagement member and to facilitate retaining the terminal within the first opening. The engagement member is configured to engage the terminal when the terminal is received within the second opening to facilitate electrically coupling the terminal to the engagement member and to facilitate retaining the terminal within the second opening.

DETAILED DESCRIPTION OF THE INVENTION

Figure 1:
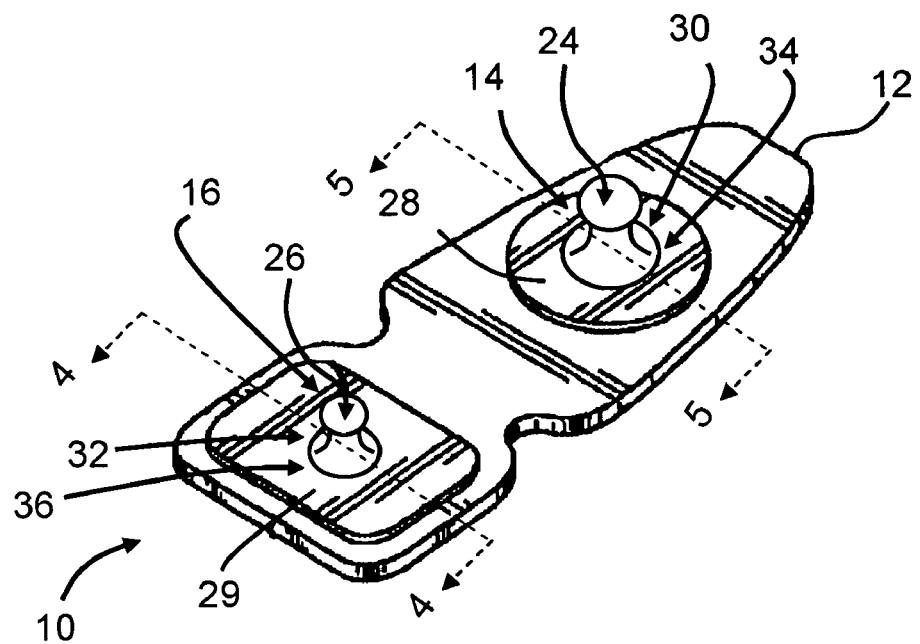
FIG. 1 is a top perspective view of an exemplary embodiment of an electrode assembly for use with a living subject.
Figure 2:
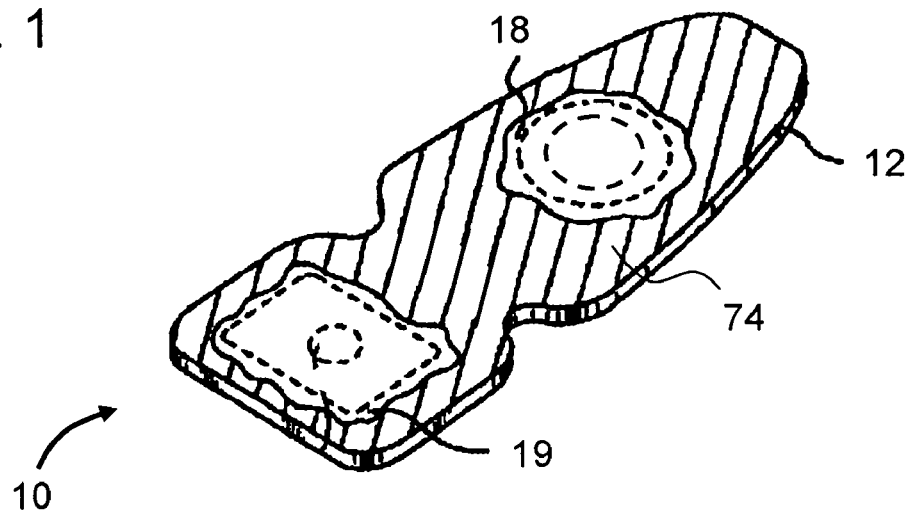
FIG. 2 is a bottom perspective view of the electrode assembly shown in FIG. 1.
Figure 3:
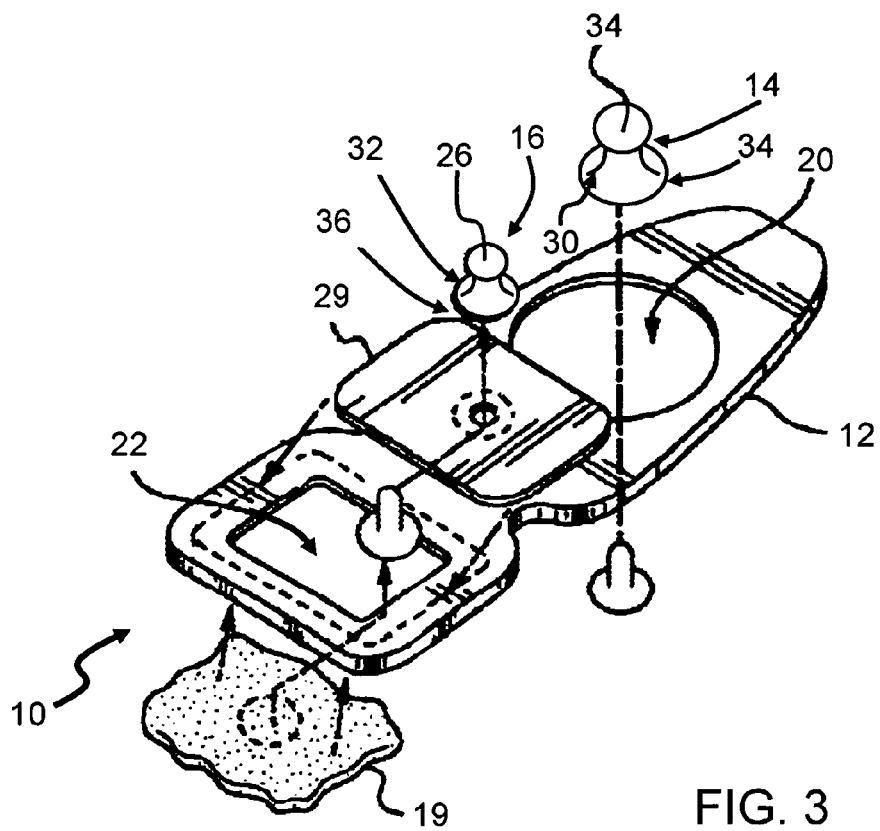
FIG. 3 is a partial exploded perspective view of the electrode assembly shown in FIG. 1.
Figure 4:
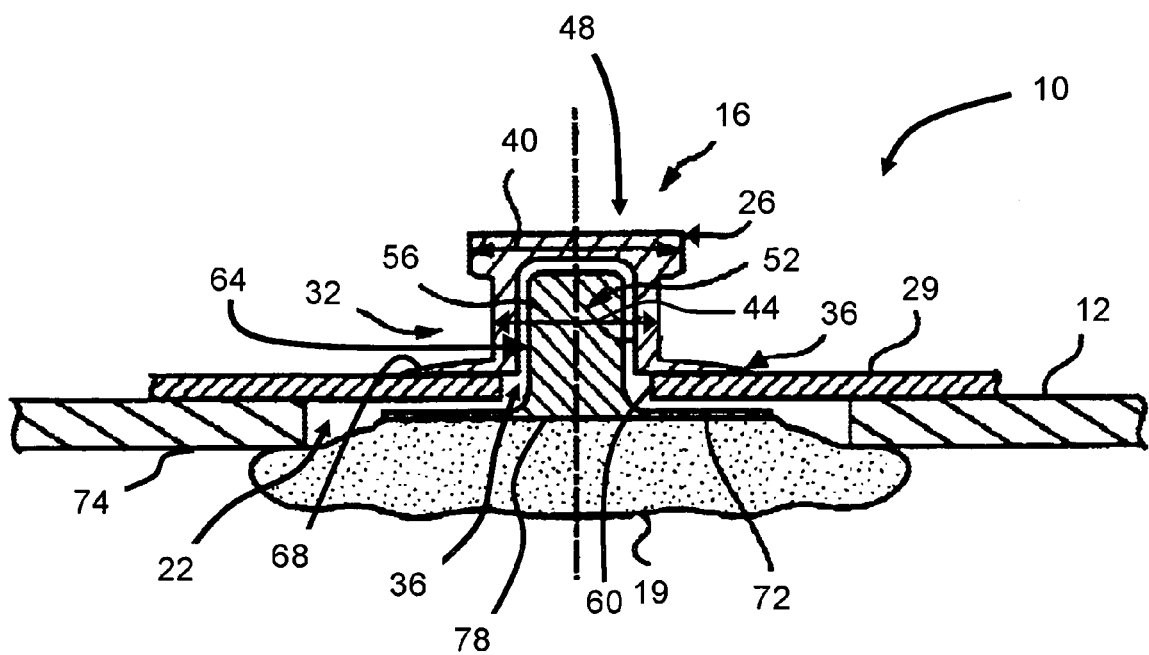
FIG. 4 is a cross-sectional view of a portion of the electrode assembly shown in FIG. 1 and taken along line 4-4.
Figure 5:
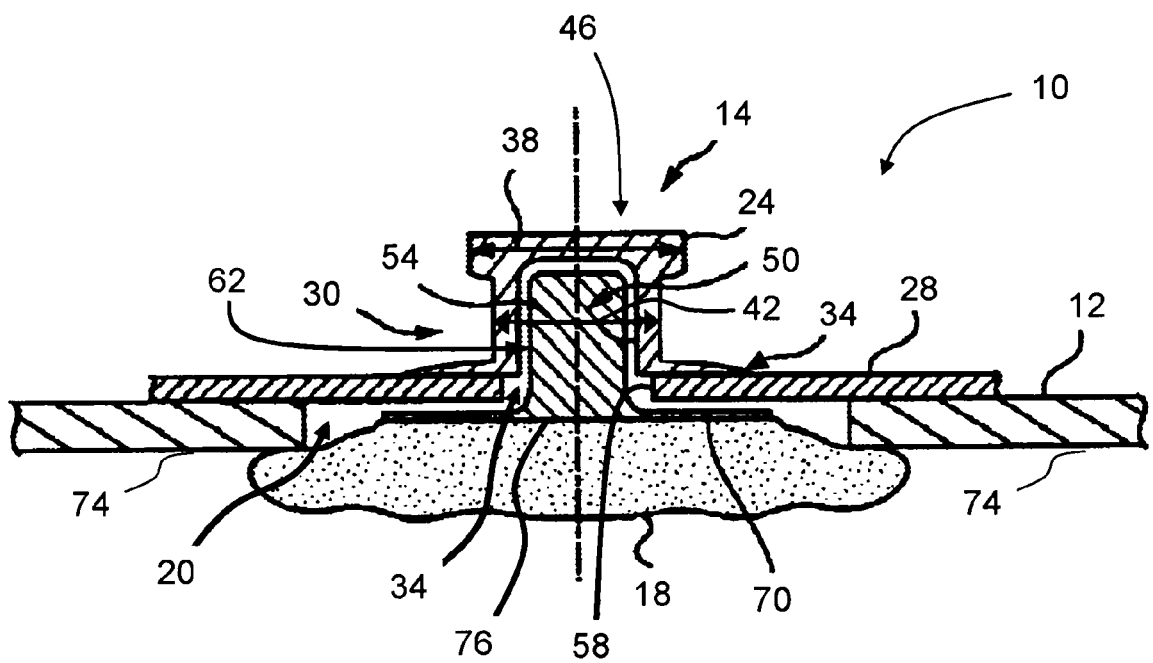
FIG. 5 is a cross-sectional view of a portion of the electrode assembly shown in FIG. 1 and taken along line 5-5.

FIG. 1 is a top perspective view of an exemplary embodiment of an electrode assembly 10 for use with a living subject (not shown in FIG. 1). FIG. 2 is a bottom perspective view of electrode assembly 10. FIG. 3 is a partial exploded perspective view of electrode assembly 10. FIG. 4 is a cross-sectional view of a portion of electrode assembly 10 taken along line 4-4 (shown in FIG. 1). FIG. 5 is a cross-sectional view of a portion of electrode assembly 10 taken along line 5-5 (shown in FIG. 1). Electrode assembly 10 generally includes a substrate 12, a plurality of terminals 14 and 16 for conducting electrical current, and a plurality of electrolytic elements 18 and 19. Although only two terminals 14 and 16 are illustrated, electrode assembly 10 may include any number of terminals. As will be describe in more detail below, terminals 14 and 16 are sized differently to facilitate coupling of components to terminals 14 and/or 16 in the correct orientation. More specifically, because terminals 14 and 16 are sized differently, terminals 14 and 16 prevent electrical cables from being inadvertently coupled to the wrong terminal 14 and/or 16.

Figure 6:
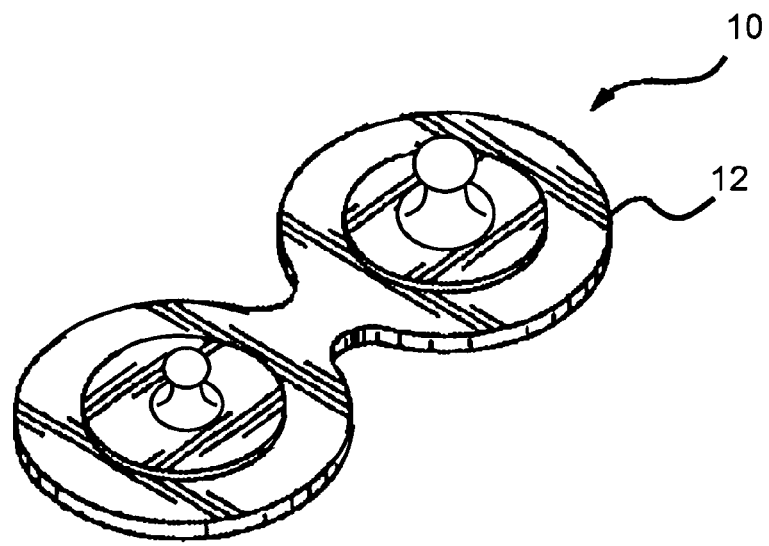
FIG. 6 is a perspective view of an alternative embodiment of the electrode assembly shown in FIG. 1.

Substrate 12 may have any suitable size and/shape, whether described and/or illustrated herein, that enables substrate 12 to function as described herein. For example, in some embodiments substrate 12 is sized and/or shaped to conform to certain physical features of the living subject. For example, in one embodiment, substrate 12 is sized, but is not limited to being sized, with a size and/or shape that conforms to the living subject's thorax, and/or a size and/or shape that conforms to the living subject's neck. Although substrate 12 may have any suitable shape, FIG. 6 illustrates one alternative example of a shape of substrate 12.

Substrate 12 may be fabricated from any suitable material(s), whether described and/or illustrated herein, that enables substrate 12 to function as described herein. For example, in some embodiments substrate 12 includes a polyethylene foam and/or a vinyl material. In some embodiments, substrate 12 is formed from a generally flexible material. The material(s) used to fabricate substrate 12 may be selected for compliance and/or flexibility to facilitate enabling substrate 12 to at least partially conform to the contours of the living subject's anatomy, while still maintaining sufficient rigidity such that terminals 14 and 16 remain in a predetermined position and orientation relative to substrate 12.

Substrate 12 includes a plurality of openings 20 and 22 that extend therethrough. Terminals 14 and 16 are received within openings 20 and 22, respectively, such that respective end portions 24 and 26 of terminals 14 and 16 extend a distance outward from and project above an upper surface 21 of substrate 12. Although substrate 12 is illustrated herein as including only two openings 20 and 22 for receiving two terminals 14 and 16, respectively, substrate 12 may include any number of openings for receiving any number of terminals. Terminals 14 and 16 may be held in position, and/or orientation, relative to substrate 12 using any suitable structure and/or means, such as, but not limited to, a respective mounting element 28 and 29 (described in more detail below). Terminals 14 and 16 may be spaced relative to each other at any suitable distance that enables terminals 14 and 16 to function as described herein. In some embodiments, wherein electrode assembly 10 includes more than two terminals, a distance between some adjacent terminals may be different that a distance between other adjacent terminals. For example, in such an embodiment, the varied spacing between terminals may facilitate enabling a clinician to select between more than one terminal spacing when coupling electrical cables to two of the terminals.

Terminals 14 and 16 may each have any size and/or shape that enables terminals 14 and 16 to function as described herein. For example, in the exemplary embodiment each terminal 14 and 16 includes a respective sidewall portion 30 and 32 that extends between a respective root 34 and 36 and the respective end portion 24 and 26. Terminals 14 and 16 generally conduct electrical current between an electrical connector (not shown in FIGS. 1-6) coupled thereto, and the respective root 34 and 36. In the exemplary embodiment, roots 34 and 36, sidewall portions 30 and 32, and end portions 24 and 26 each are fabricated with a generally circular cross-sectional shape. Although each terminal 14 and 16 may have a generally uniform cross-sectional size extending from each root 34 and 36 to each respective end portion 24 and 26, in the exemplary embodiment, end portions 24 and 26 each have a diameter 38 and 40, respectively, that is larger than a respective diameter 42 and 44 of sidewall portions 30 and 32. For example, in the exemplary embodiment, the increased diameter of end portions 24 and 26 facilitates the attachment of an electrical connector to each terminal 14 and 16.

Terminals 14 and 16 may be fabricated from any suitable material(s) that enables terminals 14 and 16 to function as described herein. For example, terminals 14 and 16 may be fabricated from, but are not limited to being fabricated from, molded and/or extruded gold, brass, or any other conductive material(s) that enables terminals 14 and 16 to function as described herein. Moreover, in other embodiments, terminals 14 and 16 are fabricated from, but are not limited to being fabricated from, an extruded metal such as but not limited to, nickel, having a metallic coating, such as, but not limited to, brass and/or gold. In another embodiment, terminals 14 and 16 are fabricated from a molded carbon terminal. In another embodiment, terminals 14 and 16 are fabricated as a molded plastic terminal having a metallic coating, such as, but not limited to, brass and/or gold. In yet another embodiment, terminals 14 and 16 are fabricated as a molded plastic terminal that has been impregnated with carbon.

Although each terminal 14 and 16 may generally be fabricated as a "one-piece" construction (possibly including a coating and/or impregnated particles), in the exemplary embodiment terminals 14 and 16 are each fabricated as a "multi-piece" construction. More specifically, in the exemplary embodiment, each terminal 14 and 16 includes a respective terminal element 46 and 48 and a separate terminal element 50 and 52, respectively. A post 54 and 56 of each respective terminal element 50 and 52 is received through an opening 58 and 60 formed within the respective mounting element 28 and 29 and is inserted into a cavity 62 and 64 defined within each respective terminal element 46 and 48. As such, each mounting element 28 and 29 is frictionally retained between a flange 66 and 68 extending from each respective terminal element 46 and 48 and a flange 70 and 72 extending from each respective terminal element 50 and 52. When fully assembled, terminal elements 46 and 50 form terminal 14, and terminal elements 48 and 52 form terminal 16. In some embodiments, terminal elements 50 and/or 52 are coated with any suitable material(s) that facilitates terminals 14 and/or 16 functioning as described herein, such as, but not limited to Ag/AgCl and/or Zinc Chloride.

Electrolytic elements 18 and 19 are each applied to a lower surface 74 of substrate 12 that is positioned against the living subject's skin. More specifically, electrolytic elements 18 and 19 are applied to surface 74 such that electrolytic elements 18 and 19 each contact the respective terminal 14 and 16. Generally, electrolytic elements 18 and 19 facilitate conducting electrical current between the respective terminal 14 and 16 and the living subject's skin. In the exemplary embodiment, electrolytic elements 18 and 19 are each applied to substrate surface 74 such that a portion of each element 18 and 19 is received within the respective substrate opening 20 and 22 and contacts a surface 76 and 78 of the respective terminal element 50 and 52. In some embodiments, a location, size, shape, configuration, and/or orientation of elements 18 and 19 relative to each respective terminal 14 and 16 may affect the accuracy of the measurement of electrical properties at terminals 14 and 16. Accordingly, in the exemplary embodiment electrolytic elements 18 and 19 are applied to substrate surface 74 such that each element 18 and 19 is oriented generally symmetrically about each respective terminal 14 and 16. However, elements 18 and 19 may each be applied to substrate surface 74 in any suitable orientation, size, shape, configuration, and/or location that enables elements 18 and 19 to function as described herein. For example, in some embodiments elements 18 and 19 may each be applied to substrate surface 74 in a non-symmetrical orientation about each respective terminal 14 and 16 to facilitate a predetermined electrolytic condition being produced, for example. Moreover, and for example, in some embodiments each element 18 and 19 may be split into a plurality of component parts.

Electrolytic elements 18 and, 19 may be formed from any suitable material(s) that enables elements 18 and 19 to function as described herein, such as, but not limited to, an ultraviolet cured potassium chloride (KCl) gel. In some embodiments, UV curing of elements 18 and 19 may facilitate a more solidified consistency and improved mechanical properties, thereby ensuring adequate adhesiveness and/or electrolytic properties are maintained while reducing excessive spreading and/or thinning of elements 18 and 19 when electrode assembly 10 is attached to the living subject's skin.

Electrode assembly 10 substrate surface 74 may include any suitable adhesive that facilitates removably attaching electrode assembly 10 to the living subject's skin. In some embodiments, electrolytic element 18 also facilitates adhesion between substrate 12 and the living subject's skin.

Electrode assembly 10 enables electrical current to be conducted between a current source (not shown in FIGS. 1-6) and the living subject's skin. For example, and although electrode assembly 10 may be used to determine other properties of the living subject, in the exemplary embodiment electrode assembly 10 is used to determine a cardiac output of the living subject, as is described in more detail below. In the exemplary embodiment, terminal 14 is a stimulation terminal that induces a potential necessary to generate electrical current flowing through a thoracic cavity (not shown) of the living subject, and terminal 16 is a measurement terminal that enables one or more electrical properties used to determine cardiac output to be measured. In operation, AC electrical current is conducted from a stimulation terminal 14 of one electrode assembly 10 attached to the living subject through the living subject's body to a stimulation terminal 14 of another electrode assembly 10 attached to the living subject. Voltage is then measured between measurement terminals 16 of the two electrode assemblies attached to the living subject.

With known electrodes, the measurement and stimulation terminals are generally fabricated with the same standard size and as such, each of such terminals may be coupled to identically sized electrical connectors (not shown in FIGS. 1-6), which are coupled to cables extending from a measurement device (not shown in FIGS. 1-6) and/or the electrical current source. As such, with known stimulation and measurement electrodes, the electrical connectors may be inadvertently coupled to the wrong terminal, such that the circuit formed by the current source, the living subject's body, and the measurement device is reversed. More specifically, with known electrodes, the electrical connector coupled to the current source may be inadvertently coupled to the measurement terminal and the electrical connector coupled to the measurement device may be inadvertently coupled to the stimulation terminal. Coupling the electrical connectors to the wrong terminals may decrease an accuracy of measurement of an electrical property, thus decreasing an accuracy of the determined cardiac output, and/or may cause mismanagement of the living subject.

To facilitate accurate measurement of electrical properties, terminals 14 and 16 are sized differently from each other. As such, and for example, a connector (not shown in FIGS. 1-6) extending from the electrical cable coupled to the current source may only be coupled to terminal 14 and a connector (not shown in FIGS. 1-6) extending from the electrical cable coupled to the measurement device may only be coupled to terminal 16. As such, terminals 14 and 16 facilitate preventing the measurement device from being inadvertently coupled to the wrong terminal. Any portion of each of terminals 14 or 16 may be sized differently from the same portion of the other terminal 14 or 16 to facilitate preventing the wrong electrical connector from being coupled to terminals 14 or 16. In the exemplary embodiment, terminal end portion 24 is sized differently than terminal end portion 26. Specifically, in the exemplary embodiment, diameter 38 of terminal 14 is larger than the corresponding diameter 40 of terminal 16. In alternative embodiments, terminal diameter 40 is larger than terminal diameter 38. It should be noted that end portion 24 of terminal 14 and end portion 26 of terminal 16 may each have any size, albeit different from each other. For example, in some embodiments the diameter 38 of terminal 14 is at least about 0.155 inches, and the diameter 40 of terminal 16 is between about 0.1 inches and about 0.155 inches. In other embodiments, the diameter 38 of terminal 14 is between about 0.18 inches and about 0.19 inches, and the diameter 40 of terminal 16 is between about 0.12 inches and about 0.13 inches. In further embodiments, and for example, the diameter 38 of terminal 14 is between about 0.1 inches and about 0.155 inches and the diameter 40 of terminal 16 is at least about 0.155 inches. For example, in other embodiments, the diameter 38 of terminal 14 is between about 0.12 inches and about 0.13 inches, and the diameter 40 of terminal 16 is between about 0.18 inches and about 0.19 inches.

Although terminal 14 is described and/or illustrated herein as a stimulation terminal and terminal 16 is described and/or illustrated herein as a measurement terminal for use determining cardiac output of a living subject, and although terminals 14 and 16 are described and/or illustrated herein as being differently sized to facilitate preventing the electrical connector coupled to the current source from being inadvertently coupled to measurement terminal 16 and/or the electrical connector coupled to the measurement device from being inadvertently coupled to stimulation terminal 14, in other embodiments terminals 14 and 16 may be differently sized to facilitate preventing the wrong electrical connector from being inadvertently coupled to terminal 14 and/or terminal 16 in any circuit at least partially formed by the living subject and terminals 14 and 16. Moreover, although terminals 14 and 16 are described and/or illustrated herein as coupled to the same substrate 12, in other embodiments, terminals 14 and 16 may each be coupled to a separate substrate.

Figure 7:
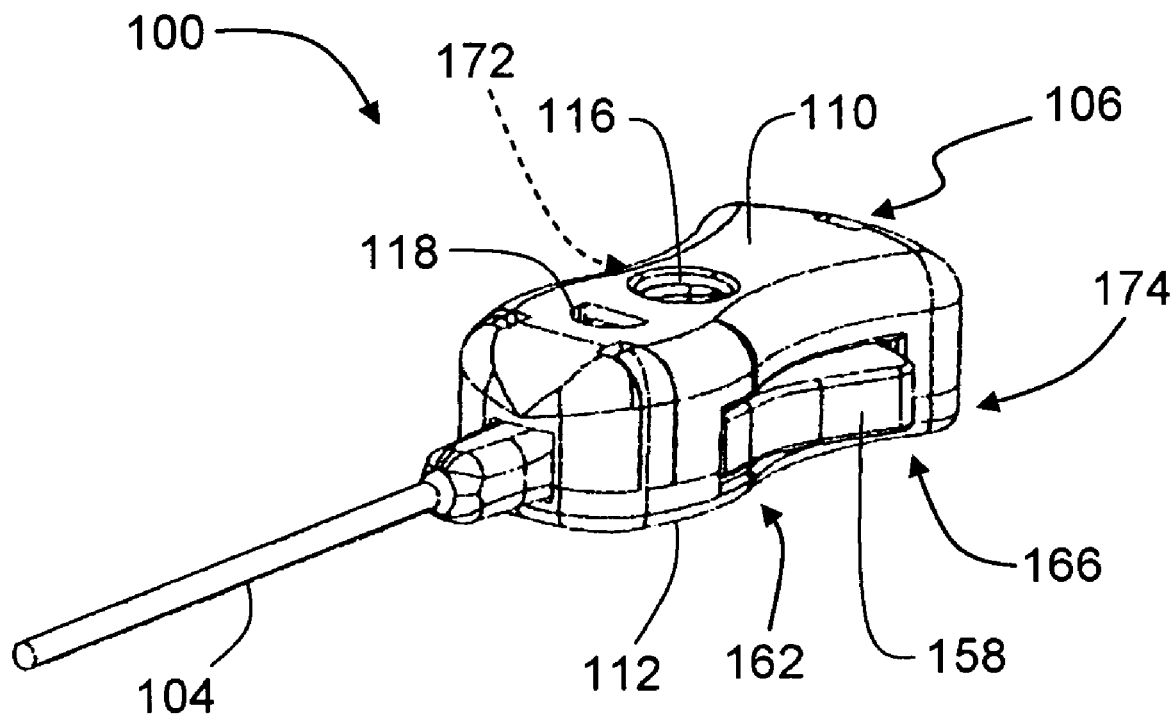
FIG. 7 is a perspective view of an exemplary embodiment of an electrical connector that may be used with the electrode assembly shown in FIG. 1.
Figure 8:
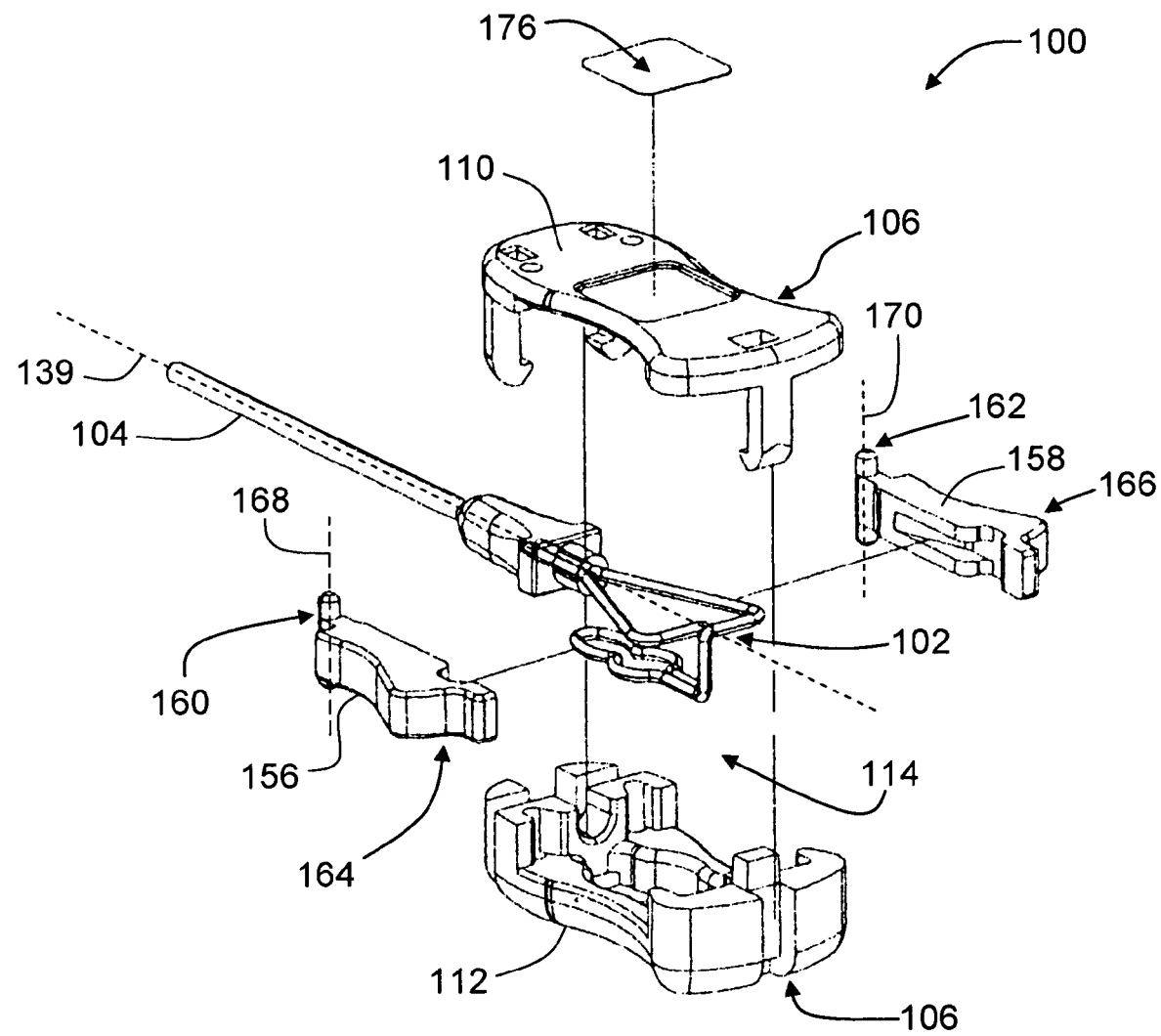
FIG. 8 is an exploded view of the electrical connector shown in FIG. 7.
Figure 9:
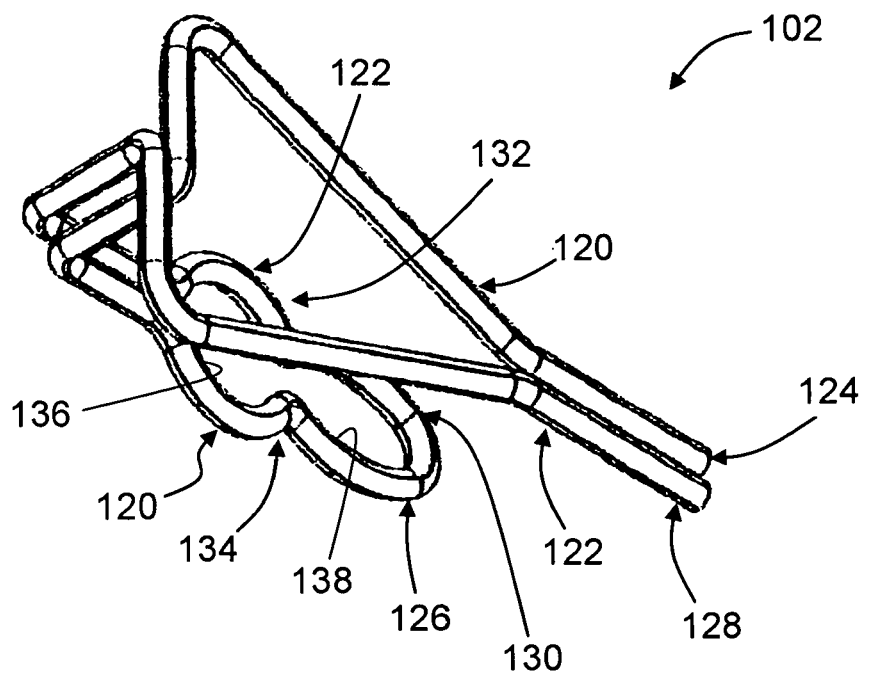
FIG. 9 is a perspective view of an exemplary embodiment of a spring used with the electrical connector shown in FIG. 7.

FIG. 7 is a perspective view of an exemplary embodiment of an electrical connector 100 that may be used with electrode assembly 10 (shown in FIGS. 1-6). FIG. 8 is an exploded view of electrical connector 100. FIG. 9 is a perspective view of an exemplary embodiment of a spring 102 used with electrical connector 100. Connector 100 facilitates electrically and mechanically coupling an electrical cable 104, such as, but not limited to, from a current source (not shown in FIGS. 7-9), and/or a measurement device (not shown in FIGS. 7-9), to a terminal, such as, but not limited to, either terminal 14 (shown in FIGS. 1-6) and/or terminal 16 (shown in FIGS. 1-6) of electrode assembly 10. Although connector 100 may be used to couple any electrical cable to any terminal, connector 100 will generally be described herein with respect to electrode assembly 10.

Connector 100 includes a housing 106, spring 102, and at least one actuator 108. In the exemplary embodiment, housing 106 includes a plurality of walls 110 and 112 that define an internal cavity 114 within housing 106. A plurality of openings 116 and 118, which will sometimes be referred to herein as holes, extend through wall 112. Holes 116 and 118 are sized to receive a portion of one terminal 14 and/or terminal 16 therein. Although only two walls 110 and 112 are illustrated, housing 106 may include any number of walls and may be fabricated to be any suitable size, shape, and/or material(s) that enables it to function as described and/or illustrated herein. Although only two holes 116 and 118 are illustrated, housing 106 may include any number of holes for receiving any number of terminals therein. Moreover, although holes 116 and 118 are illustrated and described herein as being formed within wall 112, in other embodiments, holes 116 and 118 may each be formed within wall 110 or other walls (not shown), if included.

Spring 102 is positioned within internal cavity 114 and includes a pair of arms 120 and 122. Arm 120 extends between a pair of opposite end portions 124 and 126. Similarly, arm 122 extends between a pair of opposite end portions 128 and 130. Each arm end portion 124 and 128 is coupled to electrical cable 104. In the exemplary embodiment, arm end portions 126 and 130 are coupled together. A portion 132 and 134 of each respective arm 120 and 122 defines a plurality of openings 136 and 138. In the exemplary embodiment, openings 136 and 138 are each oriented relative to a respective hole 116 and 118 to enable a portion of a terminal to be received therein. Alternatively, both openings 136 and 138 may be oriented relative to a single hole (not shown) in housing 106 that is sized to enable both openings 136 and 138 to receive a terminal extending through the hole.

Figure 10:
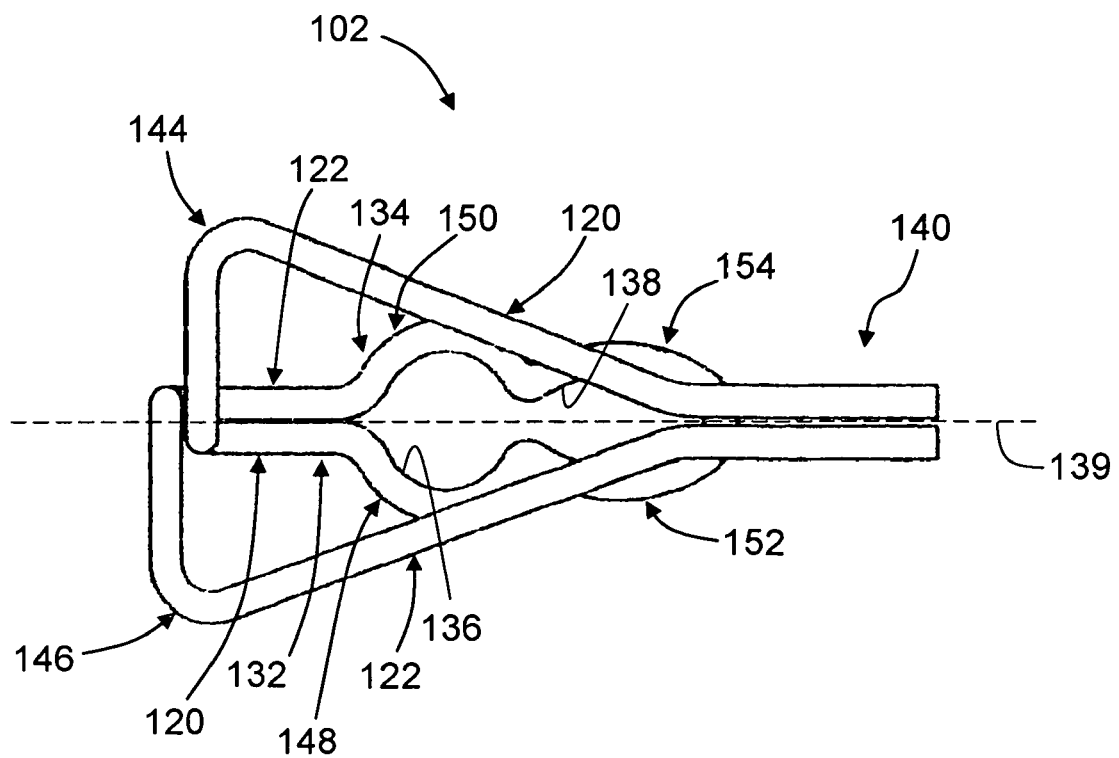
FIG. 10 is a top plan view of the spring shown in FIG. 9 and in a closed position.
Figure 11:
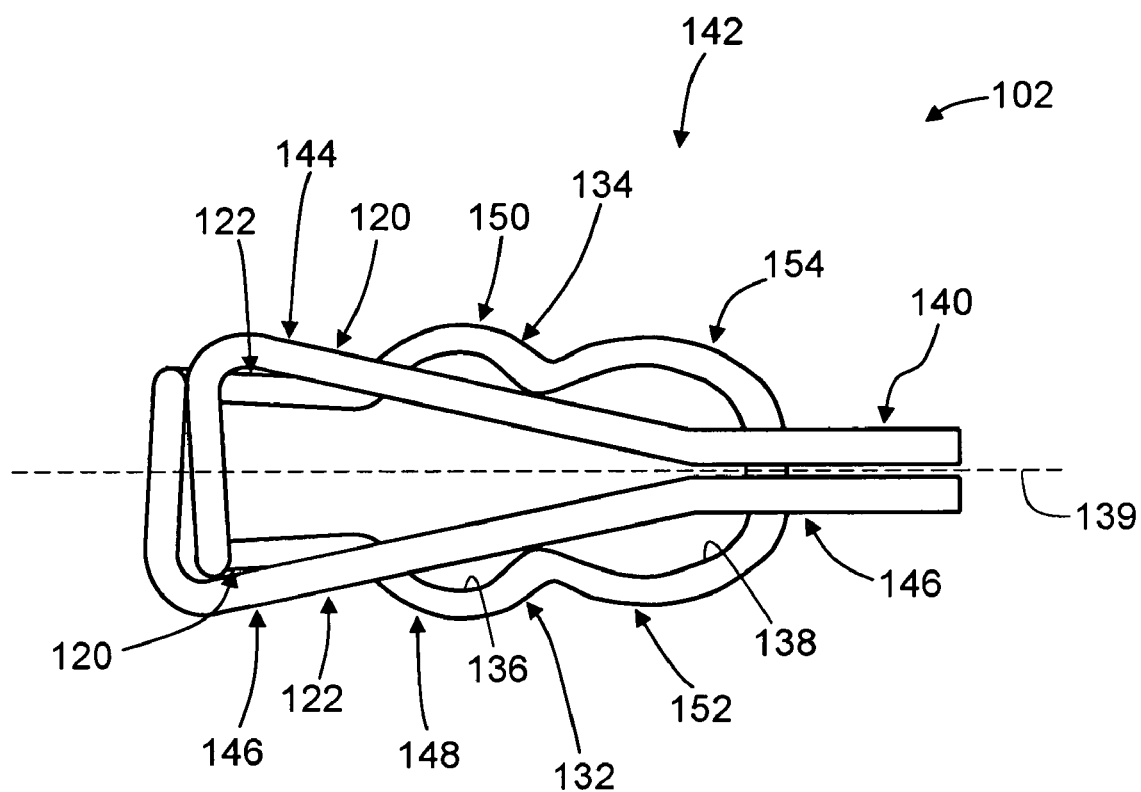
FIG. 11 is a top plan view of the spring shown in FIG. 9 and in an open position.

Spring arm portions 132 and 134 are biased towards each other and towards a central longitudinal axis 139 of connector 100 in a closed position 140, as shown in FIG. 10. Portions 132 and 134 may be moved against the bias and away from each other and axis 139 to an open position 142 illustrated in FIG. 11. In open position 142, openings 136 and 138 are each larger than when in closed position 140. In open position 142, openings 136 and 138 are each sized to enable a terminal to be received therein. Of course, in some embodiments only one of portions 132 or 134 is movable relative to axis 139 and the other portion 132 or 134.

In the exemplary embodiment, portions 132, 134 are hinged about the interconnection between end portions 126 and 130. More specifically, in the exemplary embodiment, each spring arm 120 and 122 includes a respective portion 144 and 146 that enables portions 132 and 134 to be moved generally away from each other and axis 139 to open position 142. For example, in the exemplary embodiment portions 132 and 134 are sized and shaped relative to, and interconnected with, respective portions 144 and 146, such that movement of portions 144 and 146 towards each other and axis 139 causes portions 132 and 134 to move away from each other and towards open position 142. Of course, in some embodiments only one of portions 144 or 146 is movable relative to axis 139.

In the exemplary embodiment, openings 136 and 138 are each sized and shaped to receive a portion of a respective terminal 14 and 16 therein when the respective terminal 14 and 16 extends through the respective housing hole 116 and 118. For example, in the exemplary embodiment, portions 132 and 134 each include arcuate 148 and 150, respectively that substantially mirrors a portion of terminal sidewall portion 30 to be engaged. Similarly, in the exemplary embodiment, portions 132 and 134 are formed arcuately at a respective section 152 and 154 to facilitate engaging terminal sidewall portion 32. In other embodiments openings 136 and 138 may each be sized and/or shaped to receive, and/or enable, any size and/or shape terminal to be engaged. In some embodiments, each opening 136 and 138 may be sized and/or shaped to receive differently sized and/or differently shaped terminals. For example, in the exemplary embodiment, openings 136 and 138 are each sized such that the bias of portions 132 and 134 is adjustable to accommodate any of a plurality of differently sized terminals. Although only two openings 136 and 138 are illustrated, spring 102 may include any number of openings for each receiving any number of terminals.

Spring 102 may be fabricated from any material(s) that enables spring 102 to function as described herein. For example, in some embodiments spring 102 is fabricated from, but is not limited to being fabricated from, steel and/or nickel. One specific example of spring 102 is stainless steel with nickel plating.

Although spring portions 144 and 146 may be moved using any suitable structure and/or means, in the exemplary embodiment connector 100 includes a plurality of actuators 156 and 158 coupled to housing 106 that facilitate moving portions 144 and 146 towards each other and towards axis 139. More specifically, in the exemplary embodiment actuators 156 and 158 are coupled to housing 106 such that actuators 156 and 158 engage respective portions 144 and 146 to enable movement of respective portions 144 and 146. Actuator 156 includes a pair of opposite end portions 160 and 162, and actuator 158 includes a pair of opposite end portions 164 and 166. In the exemplary embodiment, end portions 160 and 162 are rotatably coupled to housing 106 using any suitable structure and/or means that enables actuators 156 and 158 to rotate relative to housing 106 about a respective axis of rotation 168 and 170. More specifically, actuators 156 and 158 engage respective portions 144 and 146 such that rotation of end portions 162 and 166 about respective axes 168 and 170 causes portions 144 and 146 to move towards each other. In the exemplary embodiment, because portions 144 and 146 are biased away from each other towards closed position 140, actuator end portions 162 and 166 are biased away from each other to a respective position 172 and 174.

To couple a connector 100 to a terminal, spring 102 is opened by moving actuators 156 and 158 toward each other, which causes portions 144 and 146 to be moved toward each other. Simultaneously, portions 132 and 134 are moved away from each other and openings 136 and 138 are enlarged from closed position 140 to open position 142. A terminal may then be received within opening 136 or 138, and spring 102 may be released to cause portions 132 and 134 to move toward each other and into engagement with the terminal. The bias of portions 132 and 134 toward closed position 140 forces portions 132 and 134 to engage the terminal such that the terminal is electrically coupled to spring 102, and such that the terminal is retained within the opening 136 or 138. When engaged with the terminal, spring 102 may conduct electrical current between the terminal and electrical cable 104. In the exemplary embodiment, an indicator 176 is coupled to housing 106 and is electrically coupled to spring 102 to visually indicate when electrical current is conducted between electrical cable 104 and the terminal. Indicator 176 may be any suitable indicator, such as, but not limited to, a light emitting diode.

Figure 12:
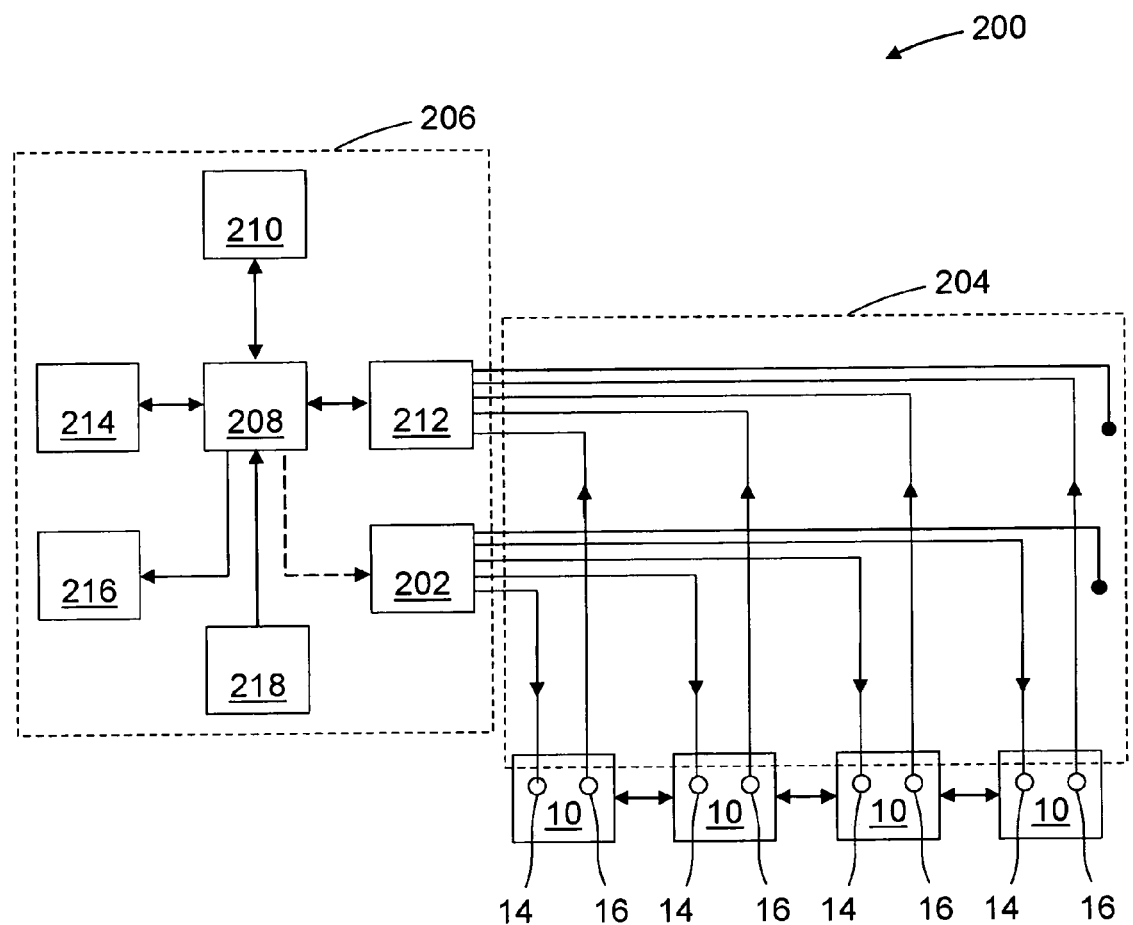
FIG. 12 is a schematic block diagram of an exemplary system for use in determining a cardiac output of a living subject.

FIG. 12 is a schematic block diagram of an exemplary system 200 used for determining a cardiac output of a living subject. System 200 includes two or more electrode assemblies 10 (shown in FIGS. 1-6), an alternating current (AC) current source 202 capable of generating a substantially constant current, an electrical cable assembly 204, and a measurement device 206. Although four electrode assemblies 10 are illustrated, system 200 may include any number of electrode assemblies 10 greater than one. Cable assembly 204 includes a plurality of electrical cables 104 for electrically connecting measurement device 206 to measurement terminal 16 of each electrode assembly and for electrically connecting current source 202 to stimulation terminal 14 of each electrode assembly 10.

Measurement device 206 includes a processor 208 having associated algorithms capable of running thereon for performing analysis of the signals measured from measurement terminals 16, one or more memories 210 in data communication with processor 208 for storing and retrieving program instructions and/or data, an I/O interface 212 (e.g., including analog-to-digital converter) for interfacing data between measurement terminals 16 and processor 208, a mass storage device 214 in data communication with processor 208 for storing and retrieving data, a display device 216 (with associated display driver, not shown) for providing an output display to a system operator, and an input device 218 for receiving input from the operator. It should be understood that processor 208, memory 210, I/O interface 212, mass storage device 214, display device 216, and input device 218 (collectively comprising the measurement device 206) may be embodied in any variety of forms, such as, but not limited to, a personal computer (PC), patient monitoring module, hand-held computer, and/or other computing device.

Figure 13:
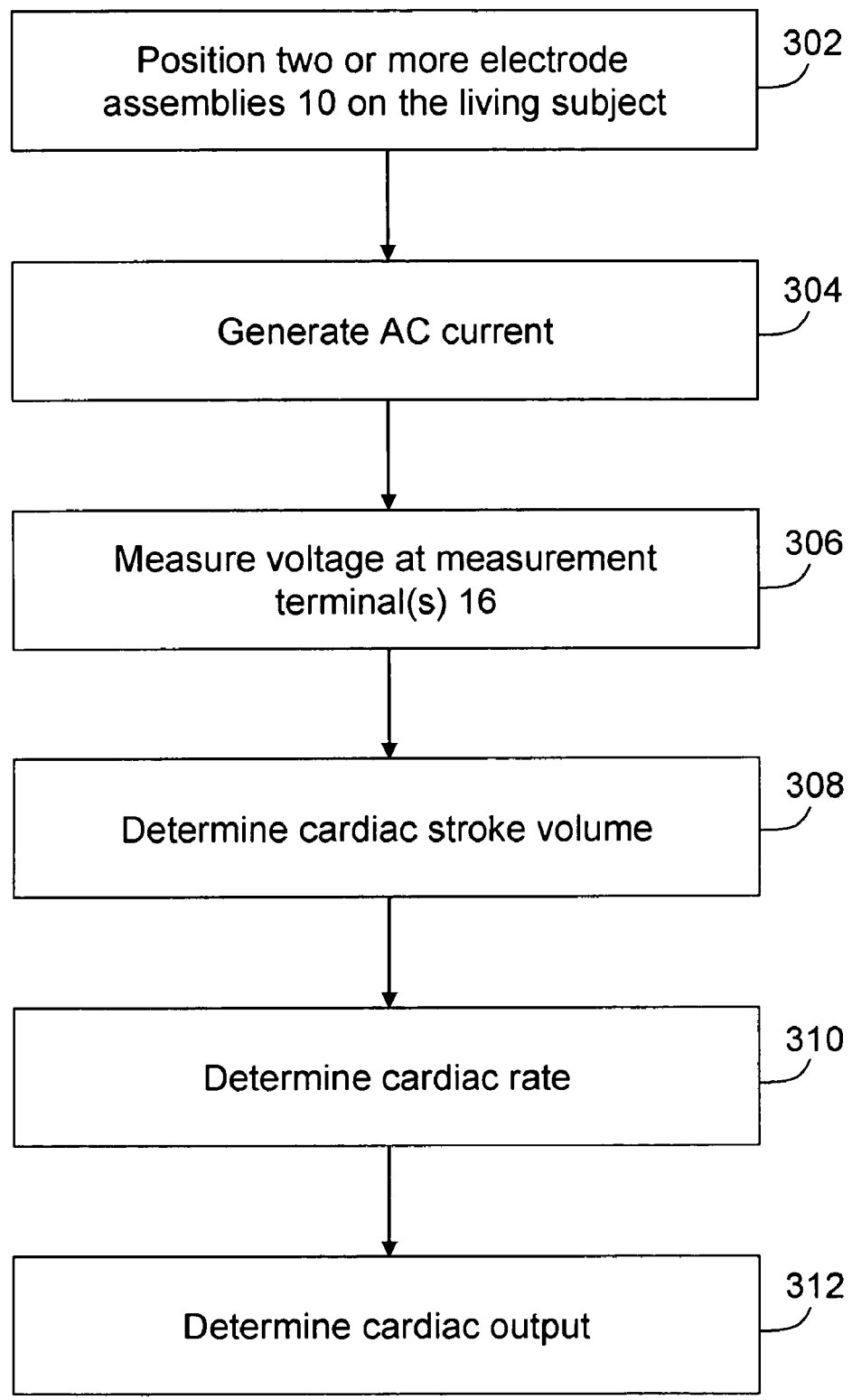
FIG. 13 is a flow chart illustrating an exemplary method for determining a cardiac output of a living subject.
Figure 14:
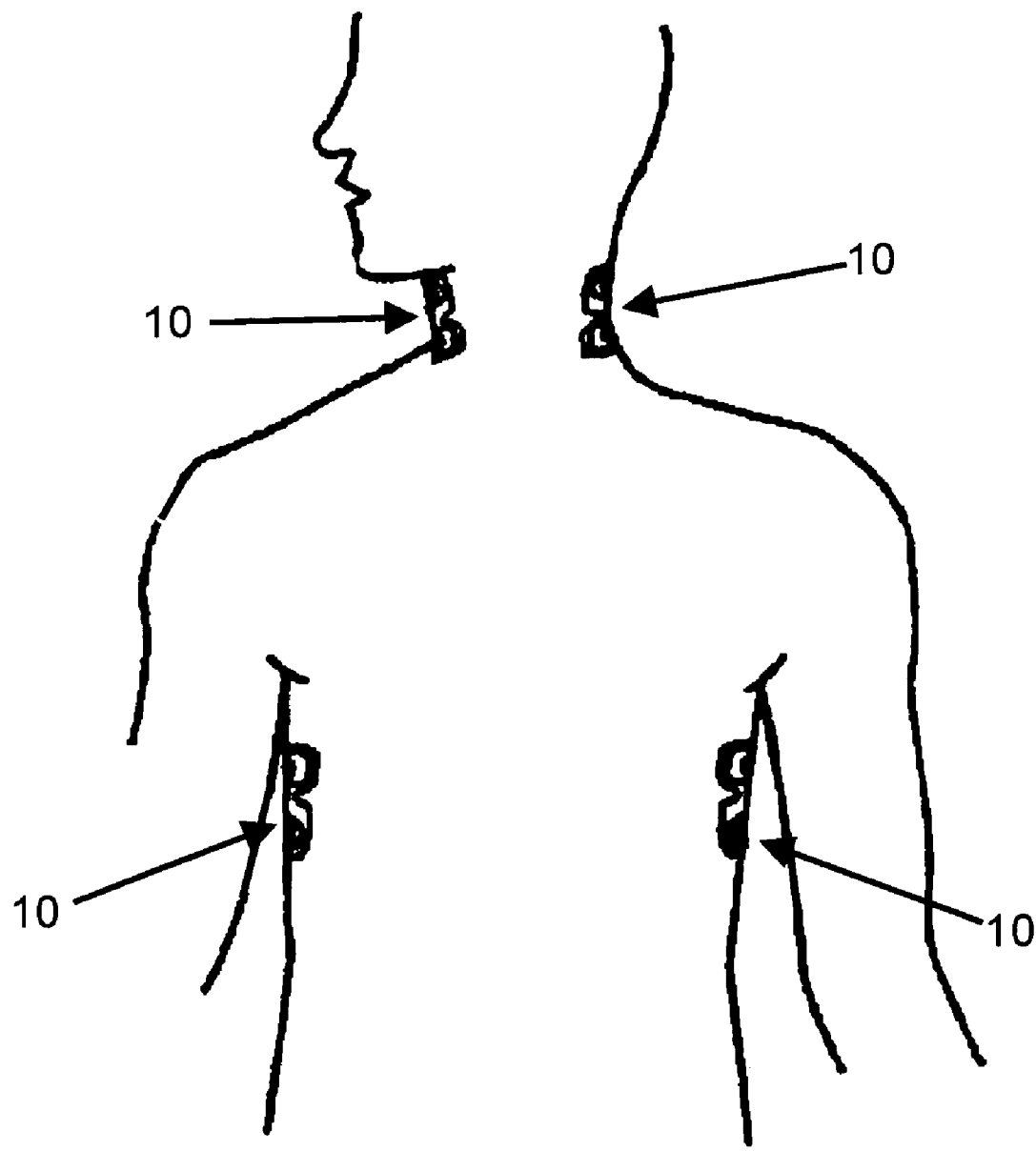
FIG. 14 is a schematic view of an exemplary human thorax having a plurality of the electrode assemblies shown in FIG. 1 attached thereto.

Although any suitable current, frequency, and/or voltage may be used, in some embodiments the applied current derived from current source 202 is about a 70 kHz sine wave of about 2.5 mA RMS and the measured voltage is about 75 mV RMS. Although cables 104 may include any suitable material(s) enabling cables 104 to function as described and/or illustrated herein, in some embodiments cables 104 include copper and/or aluminum. In some embodiments, cables 104 may be insulated using any suitable insulator, such as, but not limited to, using a polymer-based insulation. Moreover, in some embodiments a length of each of cables 104 may be selected to generally match an impedance of each of cables 104 to each other FIG. 13 is a flow chart illustrating an exemplary method 300 for determining a cardiac output of a living subject, for example using system 200 (shown in FIG. 12). Method 300 includes positioning 302 two or more electrode assemblies 10 on skin of the living subject at predetermined locations above and below the thoracic cavity of the living subject. FIG. 14 is a schematic view of a portion of an exemplary human having a plurality of electrode assemblies 10 attached thereto on a thorax and a neck of the human, although any suitable location for each electrode assembly 10 may be used. Method 300 includes generating 304 a substantially constant AC current that passes from the current source through stimulation terminal 14 of each electrode assembly 10 and the human's thoracic cavity to the stimulation terminals 14 of the other electrode assemblies 10. Voltage at each measurement terminal 16 is then measured 306, for example using measurement device 206. The voltage measured at measurement terminals 16 is generally reduced from that applied to stimulation terminals 14 by virtue of the impedance of; among other things, the thoracic cavity. In some embodiments, the measured voltage at one or more measurement terminals 16 is an absolute voltage. In some embodiments, the measured voltage at two or more measurement terminals 16 is a differential voltage. A cardiac stroke volume is then determined 308 from the measured voltage(s), for example using measurement device 206. In some embodiments, a left ventricular ejection time (LVET) and a derivative of impedance is determined, and the cardiac stroke volume is calculated based at least in part of the determined LVET and derivative of impedance. A cardiac rate is then determined 310, for example using measurement device 206. In some embodiments, the cardiac rate is determined by measuring one or more electrocardiogram (ECG) potentials using one or more measurement terminals 16, and determining the cardiac rate based at least in part on the measured ECG potential(s). Moreover, in some embodiments wherein a plurality of electrode assemblies 10 are used, measuring one or more ECG potentials includes measuring one or more body surface potentials between two measurement terminals 16 to identify one or more QRS complex events within the human, where Q, R, and S are specific fiducial points within an ECG. In some embodiments, a frequency of QRS complex events is used to determine cardiac rate. Cardiac output is then determined 312 based on the determined 308 stroke volume and the determined 310 cardiac rate, for example using measurement device 206. In some embodiments, cardiac output is determined 312 by multiplying the determined 308 stroke volume by the determined 310 cardiac rate.

By providing a plurality of differently sized and/or shaped terminals, electrode assembly 10 described and/or illustrated may facilitate preventing the wrong electrical connector from being coupled to an electrical terminal such that, for example, a circuit is reversed. More specifically, when electrode assembly 10 is used with electrical cables having differently sized connectors, the differently sized terminals of assembly 10 may facilitate preventing the wrong cable from being coupled to the wrong terminal. For example, when electrode assembly 10 used with a living subject, assembly 10 may facilitate preventing an electrical cable coupled to a current source from being inadvertently coupled to a measurement terminal and/or an electrical cable coupled to a measurement device from being inadvertently coupled to a stimulation terminal. Accordingly, electrode assembly 10 may facilitate preventing a reversal of a circuit formed by the current source, the stimulation terminal, the living subject's body, the measurement terminal, and the measurement device. Such a reversal may decrease an accuracy of a measurement by the measurement device, which may decrease an accuracy of a determined property of the living subject, and/or may cause mismanagement of the living subject. As such, electrode assembly 10 may facilitate increasing an accuracy of a measurement of by the measurement device, which may facilitate increasing an accuracy of a determined property of the living subject, and/or may facilitate management of the living subject.

By providing a spring 102 having at least one opening that includes an open position larger than a terminal, electrical connector 100 described and/or illustrated herein may facilitate reducing and/or eliminating an amount of pressure applied to the terminal, and therefore a living subject when the terminal is used therewith, used to coupled an electrical cable to the terminal. Moreover, by providing a spring having a plurality of differently sized openings, and/or providing one or more openings that are each configured to receive a plurality of differently size terminals, connector 100 may facilitate connecting the electrical cable to differently sized terminals.

Although the assemblies, systems, connectors, and methods described and/or illustrated herein are described and/or illustrated with respect to determining cardiac output of a human subject, and more specifically determining cardiac output using the thorax of the human subject, practice of the assemblies, systems, connectors, and methods described and/or illustrated herein is not limited to using the thorax of a human subject, nor determining cardiac output, nor human subjects generally. Rather, the assemblies, systems, connectors, and methods described and/or illustrated herein are applicable for determining any property of any living subject.

Exemplary embodiments of assemblies, systems, connectors, and methods are described and/or illustrated herein in detail. The assemblies, systems, connectors, and methods are not limited to the specific embodiments described herein, but rather, components of each assembly, system, and connector, as well as steps of each method, may be utilized independently and separately from other components and steps described herein. Each component, and each method step, can also be used in combination with other components and/or method steps.

When introducing elements/components/etc. of the assemblies, systems, connectors, and methods described and/or illustrated herein, the articles "a", "an", "the", "said", and "at least one" are intended to mean that there are one or more of the element(s)/component(s)/etc. The terms "comprising", "including" and "having" are intended to be inclusive and mean that there may be additional element(s)/component(s)/etc. other than the listed element(s)/component(s)/etc.

While the invention has been described in terms of various specific embodiments, those skilled in the art will recognize that the invention can be practiced with modification within the spirit and scope of the claims.

What is claimed is:

1. An electrode assembly for use with a living subject, said assembly comprising:
    a substrate having first and second openings extending therethrough;
    a first terminal at least partially received within said first opening, said first terminal comprising an end portion having a first size, at least a portion of said first terminal configured to conduct electrical current;
    a second terminal at least partially received within said second opening, said second terminal comprising an end portion having a second size that is different than said first size of said first terminal end portion, at least a portion of said second terminal configured to conduct electrical current;
    a first electrolytic element configured to transfer electrical current between the skin of a living subject and said first terminal; and
    a second electrolytic element configured to transfer electrical current between the skin of a living subject and said second terminal.

2. An assembly in accordance with claim 1 wherein said first terminal first size is larger than said second terminal second size.

3. An assembly in accordance with claim 1 wherein said first size comprises a first diameter of said first terminal end portion, and said second size comprises a second diameter of said second terminal end portion.

4. An assembly in accordance with claim 3 wherein at least one of said first terminal first diameter and said second terminal second diameter is at least about 0.155 inches.

5. An assembly in accordance with claim 3 wherein at least one of said first terminal first diameter and said second terminal second diameter is between about 0.1 inches and about 0.155 inches.

6. An assembly in accordance with claim 3 wherein said first terminal first diameter is between about 0.18 inches and about 0.19 inches, and wherein said second terminal second diameter is between about 0.12 inches and about 0.13 inches.

7. An assembly in accordance with claim 1 wherein said first and second terminals each comprise a root and a sidewall portion extending between said root and said respective end portion, a diameter of said first terminal end portion is larger than a diameter of said first terminal sidewall portion to facilitate attachment of a first electrical connector to said first terminal, and a diameter of said second terminal end portion is larger than a diameter of said second terminal sidewall portion to facilitate attachment of a second electrical connector to said second terminal.

8. An assembly in accordance with claim 1 wherein said first terminal comprises a stimulation terminal and said second terminal comprises a measurement terminal.

9. An assembly in accordance with claim 1 further comprising an attachment element coupled to said substrate and configured to removably attach said substrate to the skin of the living subject.

10. An assembly in accordance with claim 1 wherein said first terminal first size and said second terminal second size facilitate increasing an accuracy of a measurement from at least one the first and second terminals.

11. An electrical connector for electrically and mechanically coupling an electrical cable to a terminal, said connector comprising:
  a housing comprising at least one wall and an internal cavity at least partially defined by said at least one wall, said at least one wall comprising a hole for receiving at least a portion of the terminal;
  a spring positioned at least partially within said internal cavity and electrically coupleable to the electrical cable, said spring comprising first and second arms each having a first portion and a second portion, said first portions defining an opening positioned relative to said housing hole to receive at least a portion of the terminal when the terminal extends through said housing hole, said first portions biased toward each other such that said first portions engage the terminal when the terminal is received within said opening to facilitate electrically coupling the terminal to said spring and to facilitate retaining the terminal within said opening, said first and second portions configured such that when said first and second arm second portions move toward each other said first and second arm first portions move away from each other against the bias to enlarge said opening for receiving the terminal therethrough; and
  at least one actuator coupled to said housing in engagement with said first and second arm second portions, said at least one actuator configured to move said first and second arm second portions toward each other.

12. A connector in accordance with claim 11 wherein said first and second arm first portions are partially arcuate such that said opening is generally circular.

13. A connector in accordance with claim 11 wherein said spring first arm comprises a first end portion electrically coupleable to the electrical cable and a second end portion opposite the first end portion, and said spring second arm comprises a first end portion electrically coupleable to the electrical cable and a second end portion opposite the first end portion, wherein said first and second arm second end portions are coupled together.

14. A connector in accordance with claim 11 wherein said at least one actuator comprises first and second actuators, said first actuator coupled to said housing in engagement with said first arm second portion and configured to move said first arm second portion toward said second arm second portion, said second actuator coupled to said housing in engagement with said second arm second portion and configured to move said second arm second portion toward said first arm second portion.

15. A connector in accordance with claim 14 wherein said first and second actuators each comprise a first end portion rotatably coupled to said housing such that said first and second actuators each rotate with respect to said housing, and a second end portion opposite the first end portion, wherein rotation of said second end portions of said first and second actuators toward a central longitudinal axis of said connector moves said first and second arm second portions toward said central longitudinal axis.

16. A connector in accordance with claim 15 wherein said first arm second portion biases said first actuator second end away from said central longitudinal axis and said second arm second portion biases said second actuator second end away from said central longitudinal axis.

17. A connector in accordance with claim 11 wherein the terminal includes a sidewall portion extending between a root and an end portion, the end portion having a greater cross-sectional size than the sidewall portion, said first and second arm first portions each configured to engage the terminal sidewall portion.

18. A connector in accordance with claim 11 wherein said spring is configured such that said first portions are configured to engage a plurality of differently sized terminals.

19. A connector in accordance with claim 11 wherein said housing hole comprises at least one hole and said spring opening is a first opening, said spring first and second arm first portions defining a second opening positioned relative to said at least one hole to receive at least a portion of the terminal extending through said housing hole, said first portions biased toward each other such that said first portions engage the terminal when the terminal is received within said second opening to facilitate electrically coupling the terminal to said spring and to facilitate retaining the terminal within said opening, said first and second portions configured such that when said first and second arm second portions move toward each other said first and second arm first portions move away from each other against the bias to enlarge said second opening for receiving the terminal therethrough.

20. An electrical connector for electrically and mechanically coupling an electrical cable to a terminal, said connector comprising:
  a housing comprising at least one wall and an internal cavity at least partially defined by said at least one wall, said at least one wall comprising at least one hole for receiving at least a portion of the terminal; and
  an engagement member positioned at least partially within said internal cavity and electrically coupleable to the electrical cable, said engagement member comprising first and second openings each positioned relative to said at least one hole to receive at least a portion of the terminal when the terminal extends through said at least one hole, said engagement member configured to engage the terminal when the terminal is received within said first opening to facilitate electrically coupling the terminal to said engagement member and to facilitate retaining the terminal within said first opening, said engagement member configured to engage the terminal when the terminal is received within said second opening to facilitate electrically coupling the terminal to said engagement member and to facilitate retaining the terminal within said second opening.

21. A connector in accordance with claim 20 wherein said engagement member comprises a spring.

* * * * *